US011547362B2

(12) United States Patent
Seo et al.

(10) Patent No.: US 11,547,362 B2
(45) Date of Patent: Jan. 10, 2023

(54) PORTABLE TERMINAL CASE HAVING SKIN CONDITION-MEASURING FUNCTION

(71) Applicant: Amorepacific Corporation, Seoul (KR)

(72) Inventors: Jeong Eun Seo, Yongin-si (KR); Ji Hoon Kim, Yongin-si (KR); Sung Won Yi, Yongin-si (KR); Hwan Yoo, Seoul (KR)

(73) Assignee: Amorepacific Corporation, Seoul (KR)

(*) Notice: Subject to any disclaimer, the term of this patent is extended or adjusted under 35 U.S.C. 154(b) by 379 days.

(21) Appl. No.: 16/650,583

(22) PCT Filed: Sep. 27, 2018

(86) PCT No.: PCT/KR2018/011467
§ 371 (c)(1),
(2) Date: Mar. 25, 2020

(87) PCT Pub. No.: WO2019/059745
PCT Pub. Date: Mar. 28, 2019

(65) Prior Publication Data
US 2020/0229766 A1 Jul. 23, 2020

(30) Foreign Application Priority Data

Sep. 25, 2017 (KR) .................. 10-2017-0123344

(51) Int. Cl.
*A61B 5/00* (2006.01)
*A61B 5/0537* (2021.01)
*H04B 1/3888* (2015.01)

(52) U.S. Cl.
CPC .......... *A61B 5/6898* (2013.01); *A61B 5/0537* (2013.01); *A61B 5/443* (2013.01);
(Continued)

(58) Field of Classification Search
None
See application file for complete search history.

(56) References Cited

U.S. PATENT DOCUMENTS

2012/0231841 A1* 9/2012 Niederberger ....... A61B 5/6898
455/556.1
2015/0111623 A1 4/2015 Hegemier et al.
2018/0062687 A1* 3/2018 Jeon .................... H04M 1/0202

FOREIGN PATENT DOCUMENTS

CN 205039880 U 2/2016
JP 2014-176556 A 9/2014
(Continued)

OTHER PUBLICATIONS

International Search Report for PCT/KR2018/011467 dated Jan. 7, 2019 [PCT/ISA/210].
(Continued)

*Primary Examiner* — Kristy A Haupt
(74) *Attorney, Agent, or Firm* — Sughrue Mion, PLLC

(57) ABSTRACT

A portable terminal case having a skin condition-measuring function is disclosed. The case includes a battery case; a bumper case coupled to the battery case; a moisture measurement unit for receiving moisture level information in the skin of a user from a moisture measurement sensor; a contact detection unit for receiving information on the presence or absence of a contact between the bumper case and the skin from a contact detection sensor; an environment measurement unit for receiving surrounding environment information from an environment information measurement sensor; and a control unit for collecting the moisture content and the environment information from the moisture measurement unit and the environment measurement unit.

15 Claims, 6 Drawing Sheets

(52) U.S. Cl.
CPC .... *H04B 1/3888* (2013.01); *A61B 2560/0214* (2013.01); *A61B 2562/222* (2013.01); *A61B 2562/227* (2013.01)

(56) References Cited

FOREIGN PATENT DOCUMENTS

| | | |
|---|---|---|
| JP | 2016-052385 A | 4/2016 |
| KR | 10-2011-0136327 A | 12/2011 |
| KR | 10-2015-0105574 A | 9/2015 |
| WO | WO-2014006839 A1 * | 1/2014 ........... A61B 5/0531 |

OTHER PUBLICATIONS

Written Opinion for PCT/KR2018/011467 dated Jan. 7, 2019 [PCT/ISA/237].

* cited by examiner

[FIG 1]
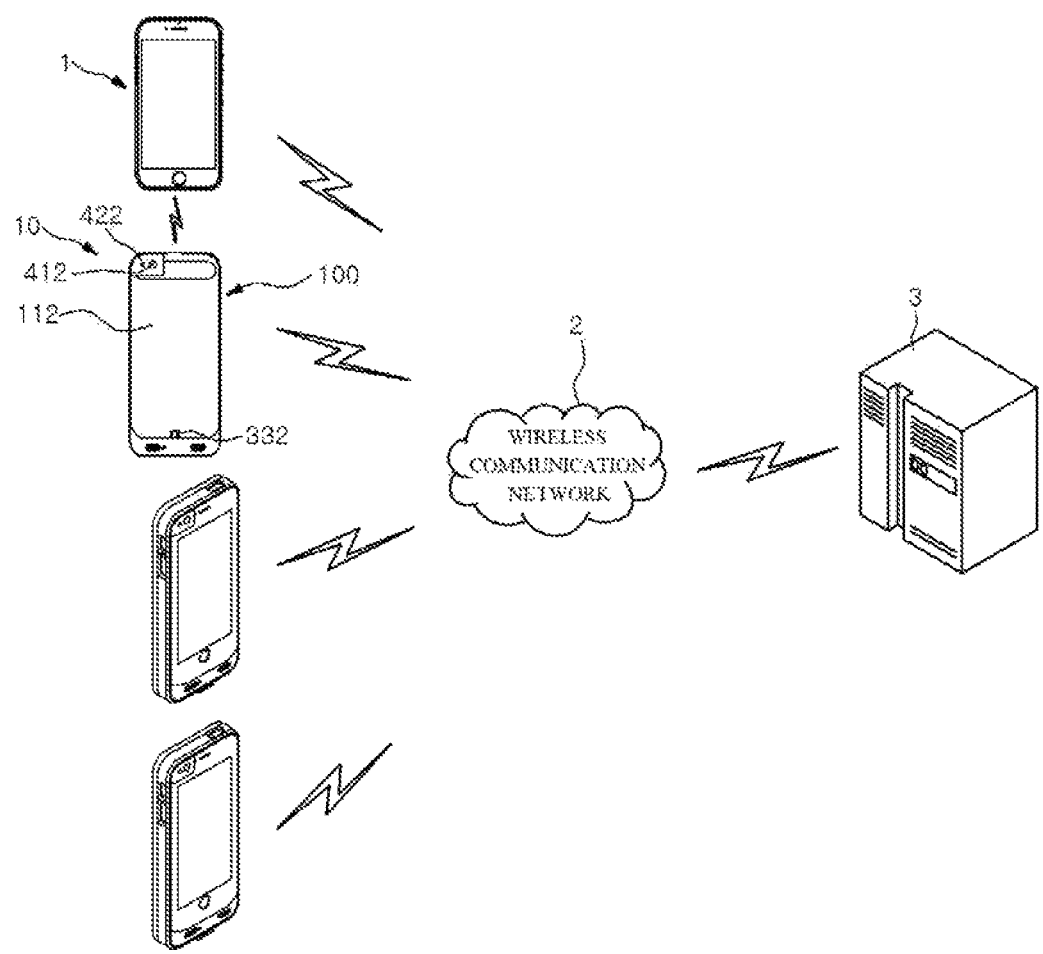

[FIG 2]
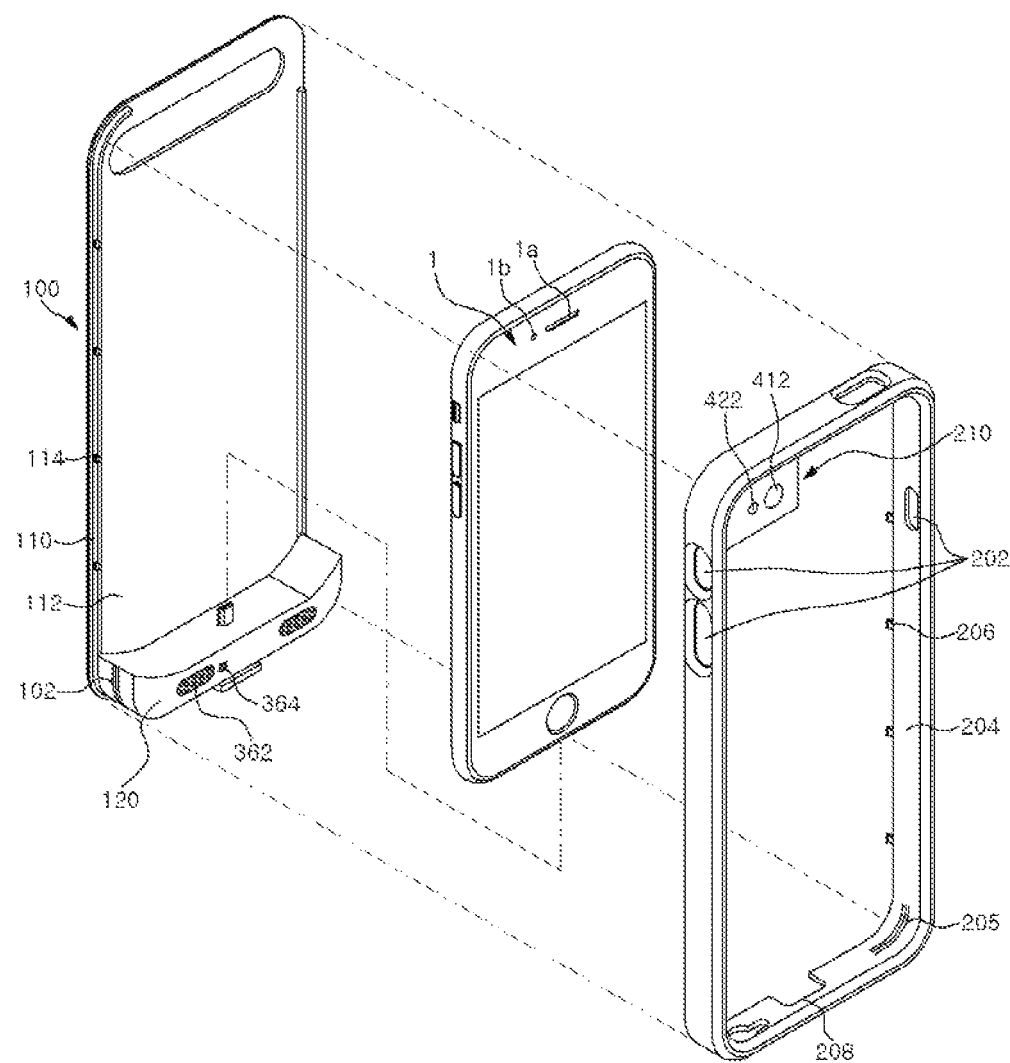

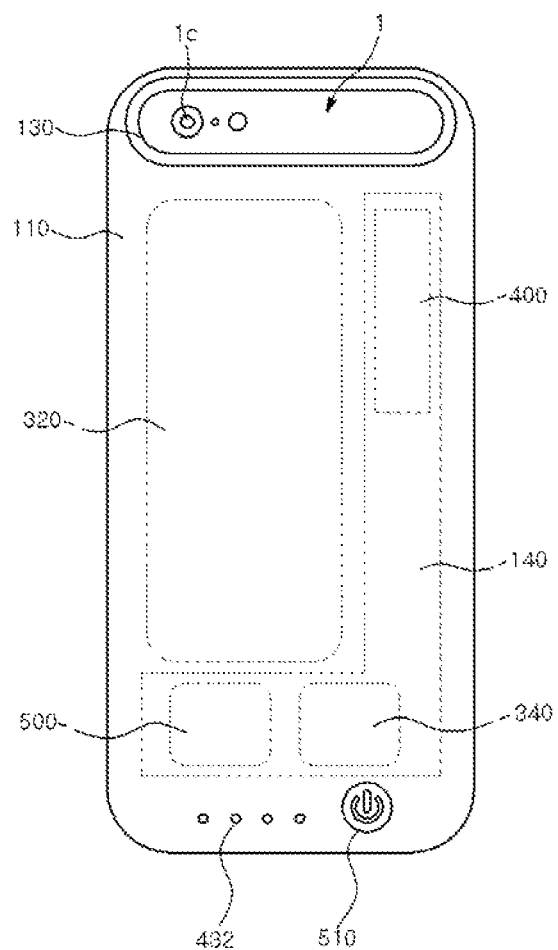
【FIG 3】

[FIG 4]
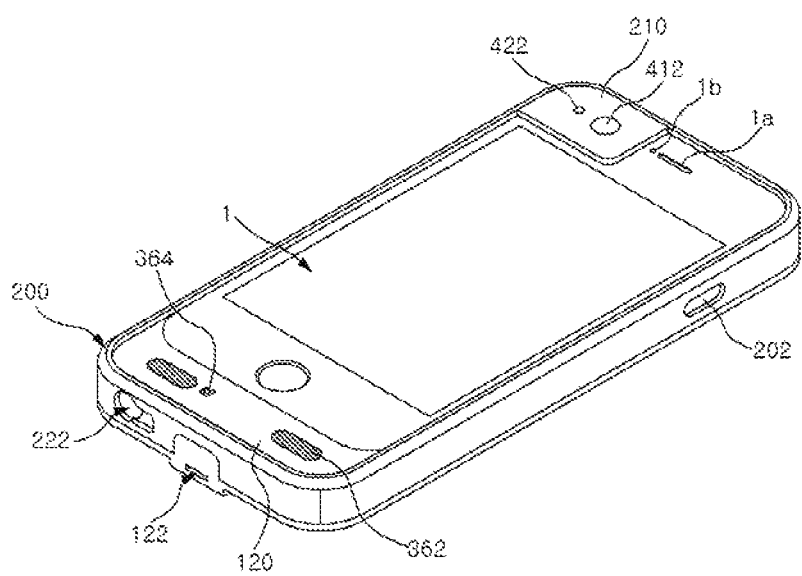

[FIG 5]
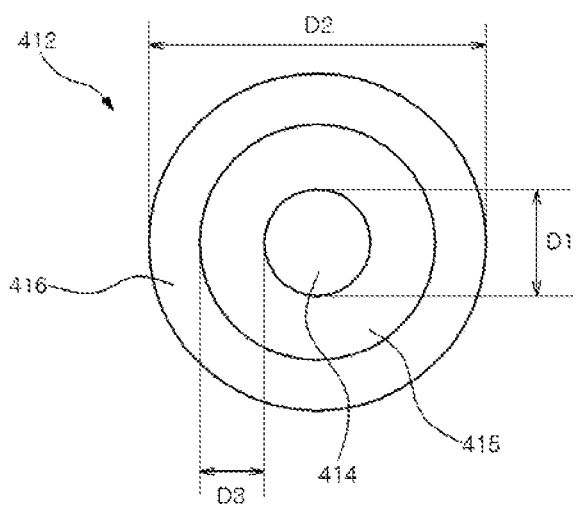

[FIG 6]
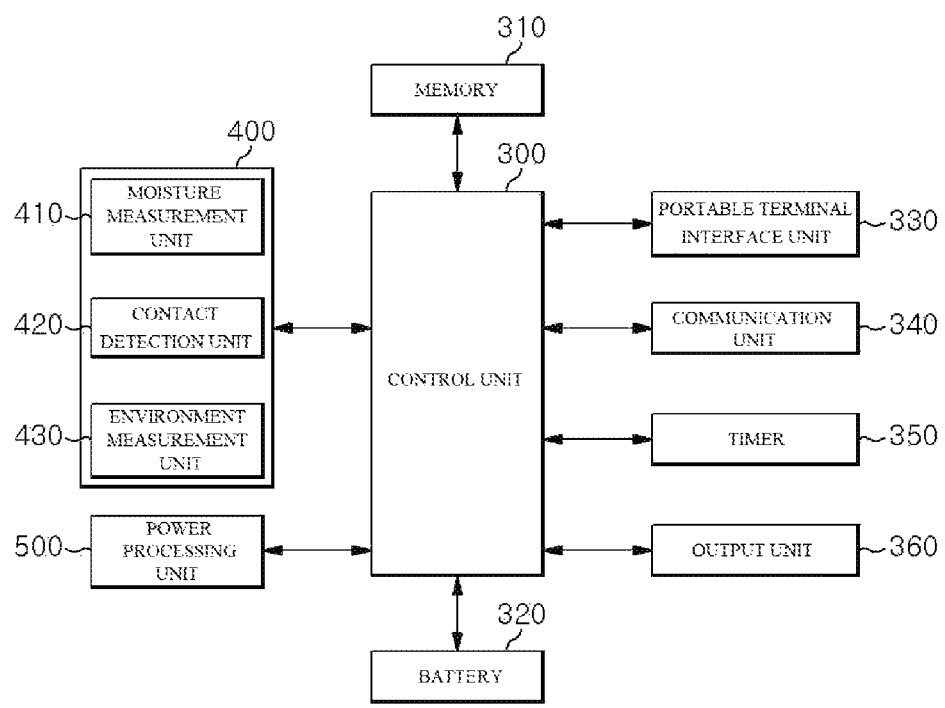

PORTABLE TERMINAL CASE HAVING SKIN CONDITION-MEASURING FUNCTION

CROSS-REFERENCE TO RELATED APPLICATION

This application is a National Stage of International Application No. PCT/KR2018/011467 filed Sep. 27, 2018, claiming priority based on Korean Patent Application No 10-2017-0123344, filed on Sep. 25, 2017 with the Korean Intellectual Property Office, the entire contents of which are hereby incorporated by reference.

TECHNICAL FIELD

The present invention relates to a portable terminal case having a skin condition measuring function.

BACKGROUND ART

In recent years, people are seeking to live in a beautiful aspect with a healthy and long life. Accordingly, interests in beauty of people are increasing day by day regardless of gender or age. In addition, the beauty industry associated with dermatology, cosmetics, etc. is also booming. Especially, with regard to skin, from treating of skin diseases to anti-aging care, people spare no time and money to maintain healthy skin and to restore healthy skin.

Meanwhile, moisturizing to the skin is most important to maintain skin health. When the skin lacks moisture, it causes complex skin aging symptoms such as skin pulling, pores and wrinkles, and it becomes difficult to maintain basic skin functions such as preventing invasion of harmful substances from the outside and suppressing evaporation of moisture in the body. Therefore, it is important to maintain and manage the moisture of the skin in daily life.

Conventionally, the skin condition may be measured by expensive equipment in a dermatology or skin care shop, but there are problems in place and cost. Recently, a small skin measuring device has been proposed. There are problems in that it is still large in size for the user to carry and use, and it is inconvenient to manage the measured results, and a complicated use procedure and a long time to measure the skin condition are required.

DISCLOSURE

Technical Problem

Embodiments of the present invention have been proposed to solve the above problems, and are intended to provide a portable terminal case having a skin condition measurement function which is convenient for a user to carry and use.

Further, the present invention is to provide a portable terminal case having a skin condition measuring function which is convenient for managing measured results.

Further, the present invention is to provide a portable terminal case having a skin condition measuring function capable of shortening a user's operation and time required for measuring a skin condition.

Technical Solution

According to an aspect of the present invention, there is provided a portable terminal case having a skin condition measuring function, comprising: a battery case having a battery therein and attached to the rear surface of the portable terminal; a bumper case coupled to the battery case and surrounding the edges of the portable terminal; a moisture measurement unit for receiving the content of moisture in the skin of a user from a moisture measurement sensor which is provided on the front surface of the bumper case and comes in contact with the skin; a contact detection unit for receiving information on the presence or absence of a contact between the bumper case and the skin from a contact detection sensor for detecting the presence or absence of the contact; an environment measurement unit for receiving surrounding environment information from an environment information measurement sensor for collecting the environment information; and a control unit for collecting the content of moisture and the environment information from the moisture measurement unit and the environment measurement unit according to the detection result of the contact detection unit.

Further, there is provided a portable terminal case having a skin condition measuring function, further comprising a communication unit configured to transmit data to a server that provides a service for managing skin condition measurement data, wherein the control unit transmits the content of moisture and the environment information to the server through the communication unit.

Further, there is provided a portable terminal case having a skin condition measuring function, wherein the communication unit further transmits data to the portable terminal, and the control unit transmits the content of moisture and the environment information to at least one of the server and the portable terminal.

Further, there is provided a portable terminal case having a skin condition measuring function, wherein the control unit transmits the content of moisture and the environment information according to a predetermined time interval.

Further, there is provided a portable terminal case having a skin condition measuring function, further comprising a portable terminal interface unit for transmitting the data and power of the battery to the portable terminal.

Further, there is provided a portable terminal case having a skin condition measuring function, wherein the portable terminal interface unit includes: a terminal provided at a lower end portion of the battery case and connected to a connection port provided at a lower side of the portable terminal; and a case connection port configured to couple to a separate cable that is connected to the connection port of the portable terminal, and wherein the battery is chargeable by the cable.

Further, there is provided a portable terminal case having a skin condition measuring function, wherein the bumper case is provided at one end of the upper side or the other side of the bumper case, and includes a bracket formed in parallel with the front surface of the portable terminal, and the moisture measurement unit and the contact detection sensor are disposed in the front surface of the bracket.

Further, there is provided a portable terminal case having a skin condition measuring function, wherein the environment information measurement sensor is disposed on the rear surface of the battery case, and the environment information measurement sensor includes a temperature sensor measuring surrounding temperature and a humidity sensor measuring humidity.

Further, there is provided a portable terminal case having a skin condition measuring function, wherein the lower end portion of the battery case is provided with a support portion for supporting the lower end portion of the portable terminal, the support portion is provided with a portable terminal interface unit for transmitting power of the battery to the portable terminal, and the environment information measurement sensor is disposed on the rear of the support portion.

Further, there is provided a portable terminal case having a skin condition measuring function, further comprising an output unit for transmitting status information to the user.

Further, there is provided a portable terminal case having a skin condition measuring function, wherein the moisture measurement sensor includes: a first electrode oscillating a predetermined frequency; a second electrode surrounding the first electrode and receiving a frequency oscillated from the first electrode; and an insulator insulating the first electrode and the second electrode, and wherein the moisture measurement sensor calculates the content of moisture based on a difference between a value oscillated at the first electrode and a value received at the second electrode.

Further, there is provided a portable terminal case having a skin condition measuring function, wherein the control unit is configured to change the frequency oscillated at the first electrode.

Further, there is provided a portable terminal case having a skin condition measuring function, wherein the control unit receives a command to change the frequency oscillated at the first electrode from the portable terminal and changes the frequency oscillated at the first electrode based on the command.

Further, there is provided a portable terminal case having a skin condition measuring function, wherein the first electrode and the second electrode are concentric, an outer diameter of the first electrode is 1.5 mm, an outer diameter of the second electrode is 6 mm, and an interval between an outer peripheral surface of the first electrode and an inner peripheral surface of the second electrode is 1 mm.

Further, there is provided a portable terminal case having a skin condition measuring function, wherein the battery is disposed long along a long side of the battery case on one side inside the battery case, and a substrate provided with the control unit is formed in an 'L' shape so as not to be overlapped with the battery and is disposed inside the battery case.

Further, there is provided a portable terminal case having a skin condition measuring function, wherein the battery case is provided with a camera hole to be corresponded to a position of the rear camera installed in the portable terminal.

Advantageous Effects

A portable terminal case having a skin condition measuring function according to the embodiments of the present invention has an advantage of being convenient for a user to carry and use.

Further, there is an effect that it is convenient to manage the measured results.

Further, there is an advantage that the user's operation and time required for measuring the skin condition may be shortened.

DESCRIPTION OF DRAWINGS

FIG. 1 is a diagram illustrating a state in which a portable terminal case having a skin condition measuring function communicates with a portable terminal and a server according to an embodiment of the present invention.

FIG. 2 is an exploded perspective view illustrating a state in which the portable terminal case and the portable terminal of FIG. 1 are coupled to each other.

FIG. 3 is the rear view illustrating the rear surface of the portable terminal case of FIG. 1.

FIG. 4 is a view illustrating a lower end portion of the portable terminal case of FIG. 1.

FIG. 5 is a diagram illustrating a configuration of the moisture measurement unit of FIG. 1.

FIG. 6 is a block diagram illustrating a configuration of a portable terminal case of FIG. 1.

BEST MODE

Hereinafter, the specific embodiments of the present invention will be described in detail with reference to the accompanying drawings.

In addition, in describing the present invention, when it is determined that the detailed description of the related known configuration or function may obscure the gist of the present invention, the detailed description thereof will be omitted.

FIG. 1 is a diagram illustrating a state in which a portable terminal case having a skin condition measuring function communicates with a portable terminal and a server according to an embodiment of the present invention, FIG. 2 is an exploded perspective view illustrating a state in which the portable terminal case and the portable terminal of FIG. 1 are coupled to each other, FIG. 3 is the rear view illustrating the rear surface of the portable terminal case of FIG. 1, FIG. 4 is a view illustrating a lower end portion of the portable terminal case of FIG. 1, FIG. 5 is a diagram illustrating a configuration of the moisture measurement unit of FIG. 1, and FIG. 6 is a block diagram illustrating a configuration of a portable terminal case of FIG. 1.

Referring to FIGS. 1 to 6, the portable terminal case 10 having the skin condition measuring function according to an embodiment of the present invention may be coupled to a portable terminal 1 to protect the portable terminal 1, and may include a battery case 100 in which a battery 320 is embedded and which is attached to the rear surface of the portable terminal 1, and a bumper case 200 coupled to the battery case 100 and surrounding the edges of the portable terminal 1.

In the present embodiment, the portable terminal 1 is described and illustrated as an example of a smart phone, but the spirit of the present invention is not limited thereto. Accordingly, the portable terminal 1 may be an electronic product having a function such as a tablet PC (portable computer), which is easily carried by a user and brought into contact with the skin, and particularly, a function of making a phone call to the face. In addition, the portable terminal 1 may be capable of data communication with the server 3 to be described later. Hereinafter, for convenience of description, the portable terminal 1 will be referred to as a smartphone 1.

The battery case 100 may include a housing 110 that is formed in a size and shape corresponding to an external shape of the smartphone 1, and a front surface of the housing 110 may be provided with a slip prevention pad 112 that provides a friction force so that the smartphone 1 is not slipped after being attached. In addition, the front of the bumper case 200 may be opened so that the front surface of the smartphone 1 may be exposed, and the rear of the bumper case 200 may also be opened so that the rear surface of the smartphone 1 coupled to the bumper case 200 may be attached to the battery case 100.

In this embodiment, an example is shown in that the smartphone 1 is first coupled to the battery case 100, and then the bumper case 200 is coupled to the battery case 100 and the smartphone 1 in the front of the smartphone 1.

Specifically, a plurality of coupling protrusions 114 may be formed around the battery case 100, and a plurality of hooks 206 may be provided around the bumper case 200 to be elastically coupled to the coupling protrusions 114. In addition, the bumper case 200 may have a size and shape corresponding to the smartphone 1 such that the edges of the smartphone 1 may be closely attached, and the smartphone 1 may be seated on a coupling portion 204 formed on the inner peripheral surface of the bumper case 200. The bumper case 200 may be formed elastically deformable material having a predetermined level for smooth coupling, and may be returned to its original state after being deformed to an appropriate level when it is coupled to or separated from the battery case 100 and the smartphone 1.

Meanwhile, in the present embodiment, an example is described in which the bumper case 200 is coupled from the front of the smartphone 1, but the spirit of the present invention is not limited thereto. For example, one side of the bumper case 200 is cut off, and a guide is formed on the inner circumferential surface of the bumper case 200 so that the smartphone 1 and the battery case 100 may be coupled in a slide manner through a cut portion. In addition, the coupling method between the bumper case 200 and the smartphone 1 and the battery case 100 is not limited to the above-described method using the coupling protrusion 114, the hook 206, and the like. Accordingly, the various methods may be applied, such as being formed to surround the entire edges of the smartphone 1 and the battery case 100 by the bumper case 200.

Meanwhile, the contact portions of the battery case 100 and the bumper case 200 may be formed with the electrodes 102 and 205, respectively, and may be configured to transmit and receive power, data, and electrical signals by being electrically connected to each other. In the present embodiment, the electrodes 102 of the battery case 100 may be formed at both sides of the support portion 120 to be described later, and the electrode of the bumper case 200 may be formed to correspond to the electrode 102 of the battery case 100. The position, shape, and manner of the electrodes are not limited thereto although illustrated as being in contact with each other as an example.

The portable terminal case 10 may include a sensor unit 400 for measuring a skin condition of a user and collecting surrounding environment information. Specifically, the sensor unit 400 may include a moisture measurement unit 410 for receiving the content of moisture in the skin of a user from a moisture measurement sensor 412 which is provided on the front surface of the bumper case 200 and comes in contact with the skin, a contact detection unit 420 for receiving information on the presence or absence of a contact between the bumper case 200 and the skin from a contact detection sensor 422 for detecting the presence or absence of the contact, and an environment measurement unit 430 for receiving surrounding environment information from an environment information measurement sensor 432 for collecting the environment information.

The moisture measurement unit 410 and the contact detection unit 420 may be disposed in the front surface of the bumper case 200, such that the moisture state of the skin may be conveniently measured in the same manner as the user uses the smartphone 1 for a phone call.

Specifically, one end of the upper side or the other side of the bumper case 200 may be provided with a bracket 210 formed in parallel with the front surface of the smartphone 1, the moisture measurement sensor 412 and the contact detection sensor 422 may be disposed in the front surface of the bracket. In the present embodiment, the upper side means an upper side direction based on FIG. 2, as a direction in which the receiving speaker 1a of the smartphone 1 is arranged. In addition, in the present embodiment, the lower side means a lower side direction on FIG. 2 in which a cable connection port of the smartphone 1 is formed as a position facing the upper side.

In this case, the bracket 210 may be formed to be attached with the front surface of the smartphone 1 to be stably supported. In addition, the moisture measurement unit 412 and the contact detection sensor 422 provided to the bracket 210 may be electrically connected with a substrate 140 and the battery 320 provided to the battery case 100 through the terminal 205 provided to the bumper case 200, and may transmit a signal to the moisture measurement unit 410 and the contact detection unit 420. To this end, a conductive wire (not shown) connecting the moisture measurement sensor 412 and the contact detection sensor 422 to the terminal 205 may be provided inside the bumper case 200.

In this embodiment, the bracket 210 is shown as an example formed on left side of the front surface of the smartphone 1, and may have a size and shape that does not cover a camera 1b of the front surface and a display area of the smartphone 1.

Herein, the moisture measurement sensor 412 may include a first electrode 414 oscillating a predetermined frequency, a second electrode 416 surrounding the first electrode 414 and receiving a frequency oscillated from the first electrode 414, and an insulator 415 that insulates the first electrode 414 and the second electrode 416. In this case, the first electrode 414 and the second electrode 416 may be concentric. In addition, the outer diameter D1 of the first electrode 414 may be set to 1.5 mm, the outer diameter D2 of the second electrode 416 may be set to 6 mm, and an interval D3 between an outer circumferential surface of the first electrode 414 and an inner circumferential surface of the second electrode 416 may be set to 1 mm. Moreover, a thickness exposed to the outside of the first electrode 414 and the second electrode 416 may be formed to be 0.8 mm or less. When the frequency and the electrodes 414 and 416 are used, the skin content may be measured more accurately and the moisture measurement sensor 412 may be miniaturized, such that the heterogeneity may be reduced even if the moisture measurement sensor 412 is in contacted to the skin.

As such, the moisture measurement sensor 412 may calculate the content of moisture of the skin according to the difference between a frequency value oscillated by the first electrode 414 and a frequency value received by the second electrode 414. Specifically, the frequency oscillated at the first electrode 414 may not be directly transmitted to the second electrode 416 by the insulator 415, and may be transmitted to the two electrodes 416 only through the skin of the user to which the moisture measurement sensor 412 is in contacted. However, a dielectric constant of the skin may be varied according to the skin condition of the user, in particular, the content of moisture of the skin, and an amount of frequency attenuation may be varied according to the dielectric constant of the user's skin when the frequency passes through the user's skin. In other words, the frequency measured by the second electrode 416 may be varied according to the content of moisture of the user's skin. The moisture measurement unit 416 may calculate the content of moisture of the skin according to an amount of frequency change. To this end, the matching data of amounts of frequency change and contents of moisture for specific frequencies may be stored in the memory 310.

In this case, the frequency oscillated by the first electrode 414 may be varied by a control unit 300. That is, the control unit 300 may change the frequency oscillated from the first electrode 414 according to the manufacturer's setting or the user's setting. For this purpose, the portable terminal case 10 may further include an operation unit (not shown) that allows the user to select a frequency.

Meanwhile, the contact detection sensor 422 may be disposed adjacent to the moisture measurement sensor 412. In this regard, in an event where a contact with the user's skin is detected from the contact detection sensor 422, the contact detection sensor 422 may also be disposed close to the moisture measurement sensor 412 enough to be considered in contact with the user's skin in an extent that the moisture measurement sensor 412 may also be considered in contact with the user's skin. As an example, the contact detection sensor 422 may be disposed within a few millimeters from the moisture measurement sensor 412, and may be provided in parallel with the front surface of the bracket 210 as described above.

The contact detection sensor 422 may be various known sensors such as a pressure sensor, a distance sensor, and an optical sensor, but the spirit of the present invention is not limited to the type of the contact detection sensor 422. Further, the moisture detection sensor 412 and the contact detection sensor 422 may be connected to the control unit 300 and the substrate 140 in a UART (Universal Asynchronous Receiver-Transmitter) communication method. In addition, the moisture detection sensor 412 and the contact detection sensor 422 may be connected in parallel to one line extending from the substrate 140, but the spirit of the present invention is also not limited to the communication method and connection method.

The environment information measurement sensor 432 may be for obtaining the surrounding environment information of the portable terminal case 10, such as for measuring temperature and humidity. That is, the environment information measurement sensor 432 may include a temperature sensor capable of measuring surrounding temperature and a humidity sensor capable of measuring surrounding humidity, and according to an embodiment, the environment information measurement sensor 432 may include a sensor in which the temperature sensor and the humidity sensor may be integrally formed. Since the skin condition of the user, in particular, the content of moisture is greatly affected by the temperature and humidity of the surrounding environment, if the temperature and humidity of the surrounding environment may be measured and stored together with the content of moisture of the skin obtained through the moisture measurement sensor 412, more specific and detailed monitoring of the skin condition may be possible. According to an embodiment, the environment information measurement sensor 432 may further include additional sensors in addition to the above-described temperature sensor and humidity sensor.

Herein, the environment information measurement sensor 432 may be provided to the battery case 100, specifically, may be provided at a point on the rear surface of the battery case 100. In this embodiment, the environment information measurement sensor 432 is shown as an example which is formed on the lower end portion of the battery case 100 and provided on the back of the support portion 120 that may support the smart phone 1. In this case, the battery case 100 may be formed with a plurality of ventilation holes to accurately measure the surrounding environment information such as temperature and humidity, and the environment information measurement sensor 432 may be disposed inside the ventilation hole.

In addition, the portable terminal case 10 may further include a control unit 300 that collects the content of moisture and environment information of the skin from the moisture measurement unit 410 and the environment measurement unit 430 according to the detection results of the contact detection unit 420. When the control unit 300 receives a result that the user's skin is in contacted with the bumper case 200, specifically, the bracket 210, from the contact detection unit 420, it determines that the moisture measurement sensor 412 is also in contacted with the user's skin, and transmit a signal to collect data from the moisture measurement sensor 412 to the moisture measurement unit 410. In this case, the determination that it has come into contact with the user's skin may be made by additionally determining a condition such as the contact state being continued above a predetermined time or being detected above a predetermined pressure, or the like. In addition, the control unit 300 may measure the skin condition and store the result only when the condition is satisfied.

Further, the control unit 300 may transmit a signal to collect data from the environment information measurement sensor 432 to the environment measurement unit 430. In this case, the collection of environment information by the control unit 300 may be performed according to the detection result of the contact detection unit 420 like the moisture measurement sensor 412. That is, the control unit 300 may collect the surrounding environment information when measuring the content of moisture of the skin. In addition, the control unit 300 may collect environment information according to a predetermined time interval, and the collected information may be provided to the smartphone 1 or the server 3 apart from the moisture measurement result.

In the present embodiment, while the control unit 300, the moisture measurement unit 410, the contact detection unit 420, and the environment measurement unit 430 are described independently, they may be functionally divided and processed modules, or one physical configuration, for example, which is functionally implemented in an MCU. Further, the moisture measurement unit 410 may include the moisture measurement sensor 412 or be understood as substantially the same concept as the moisture measurement sensor 412, and the contact detection unit 420 may include the contact detection sensor 422 or be understood as substantially the same concept as the contact detection sensor 422. The environment measurement unit 430 may include the environment information measurement sensor 432 or be understood as substantially the same concept as the environment information measurement sensor 432.

Meanwhile, the portable terminal case 10 may further include a communication unit 340 capable of transmitting data, specifically, information which is collected from a moisture measurement unit 410 or an environment measurement unit 430, to the server 3. Herein, the server 3 may provide a service that may manage skin condition measurement data, and may be operated by various entities such as a manufacturer/supplier of the portable terminal case 10, a mobile communication service provider, and a cosmetic manufacturer/supplier. Further, data managed by the server 3 may be provided to a user through an environment such as a smartphone 1 or a PC. To this end, the smart phone 1 or the PC may be connected to the server 3 through a wireless communication network 2 or a wired communication network, and may provide data received from the portable terminal case 10 to the server 3, or may receive from the server 3.

Herein, the communication unit 340 may be connected to the server 3 through the wireless communication network 2. The wireless communication network 2 may be understood to include all of wireless environments in which the portable terminal case 10 may be directly connected to the server 3, wireless environments (e.g., WIFI, BLE, BLUETOOTH, NFC, ZIGBEE, etc.), which may be connected to the server 3 via a wireless Internet network and a wired Internet network provided by a mobile communication service provider, and the like. For example, the wireless communication network 2 may be a dedicated network for an IoT (Internet of Things) provided by the mobile communication service provider, and the communication unit 340 may include a wireless communication chip and antenna capable of communicating with such the dedicated network.

The control unit 300 may store the content of moisture and environment information, which is data collected from the moisture measurement unit 410 and the environment measurement unit 430, into the memory 310, or may transmit data to the server 3 through the communication unit 340. The server 3 may store data provided from the portable terminal case 10 in its own database, and then provide it to the customers through a predetermined program or application installed on a PC or smartphone 1 used by the user.

In this case, the communication unit 340 may also transmit the data to the smartphone 1. To this end, the smart phone 1 may be provided with a communication unit having a standard for data communication with the communication unit 340. In this case, the control unit 300 may transmit the content of moisture and environment information to one or both of the server 3 and the smartphone 1, which may vary depending on the service provided by the server 3.

In particular, an application for showing data provided from the portable terminal case 10 to the user may be installed in the smartphone 1. In addition, the application installed in the smart phone 1 may have a function of receiving and storing data provided from the portable terminal case 10 even when the corresponding application is inactive.

Herein, the portable terminal case 10 may be further provided with a timer 350 for checking the passage of time, and the control unit 300 may transmit the content of moisture and environment information to the smartphone 1 and the server 3 according to a predetermined time interval based on the values provided from the timer 350.

Meanwhile, the battery case 100 may further include a portable terminal interface unit 330 for transferring the power of the battery 320 to the smartphone 1. Specifically, the portable terminal interface unit 330 may further include a terminal 332 provided on the lower end portion of the battery case 100 and connected to a connection port provided on the lower side of the smartphone 1, and a case connection port 122 that may be connected to a separate cable (for example, a charging cable) for power charging and data communication that may be connected to the connection port of the smartphone 1. The terminal 332 and the portable terminal interface unit 330 may be configured to transmit the power of the battery 320 to the smartphone 1 or directly transmit an external power provided through the case connection port 122 to the smartphone 1. Further, the battery 320 may be charged by electric power supplied through a cable connected to the case connection port 122. By such a configuration, the user may use the smartphone 1 for a longer period of time in a state where the portable terminal case 10 is coupled to the smartphone 1, and the portable terminal case 10 and the smartphone 1 may also be conveniently charged. In this case, the bumper case 200 may be formed with a groove 208 into which the lower end portion of the battery case 100 provided with the case connection port 122 is fitted, whereby it is possible to prevent the thickness of the entire case 10 from being thickened, even if the case connection port 122 is provided.

Herein, the terminal 332 may transmit data as well as the power of the battery 320 to the smartphone 1 or data from the smartphone 1 to the portable terminal case 10. For example, the control unit 300 may transmit the content of moisture information and environment information to the smartphone 1 through the communication terminal 340 as well as the portable terminal interface unit 330. Of course, the above information may also be transmitted to the smart phone 1 through only the portable terminal interface unit 330.

In addition, the user may control the portable terminal case 10 by manipulating the application provided in the smartphone 1, where the necessary data may be transferred from a smartphone 1 to the control unit 300 through the portable terminal interface unit 330 and/or communication unit 340. For example, the user may issue a moisture measurement command or an environment information measurement command through the application of the smartphone 1, and the control unit 300 may perform a predetermined operation according to a command transmitted from the smartphone 1.

In addition, the user may change the frequency oscillated through the first electrode 414 by operating the application of the smartphone 1. For example, the application of the smart phone 1 may provide the user with multiple frequencies having high performance for the measurement of the content of moisture according to a predetermined condition such as the user's skin type, and when the user selects a specific frequency, the application of the smart phone 1 may transmit the corresponding frequency to the portable terminal case 10. The control unit 300 may then change the frequency oscillated through the first electrode 414 according to the frequency value received from the smartphone 1. Accordingly, the user has the advantage of being able to directly test and select a frequency suitable for measuring his skin condition at the same time, and the manufacturer has the advantage of providing customized services to various customers with one product.

Meanwhile, the lower end portion of the battery case 100 may be provided with a support portion 120 in which the lower end portion of the smartphone 1 is contacted and supported. In addition, the terminal 332 may be provided on the upper side of the support portion 120.

In addition, a switch 510 for manipulating the power of the portable terminal case 10 may be provided on the rear surface of the support portion 120. The power processing unit 500 may be connected to the switch 510 to selectively control whether the power supplied from the battery 320 or through a separate cable is supplied or charged to the entire device. In this case, the portable terminal case 10 may be switched to a standby mode when there is no use for a certain period of time even if the power is ON. Then, the portable terminal case 10 may be operated only when a user's skin contact is detected or only when the communication with the smartphone 1 and the server 3 is made.

In addition, the battery case 100 and the bumper case 200 may be provided with an output unit 360 for transmitting the status information of the portable terminal case 10, such as the remaining amount of the battery 320 and the operation state of a sensor unit 400, to the user. In this embodiment, it is illustrated as an example where a speaker 362 capable of audibly transmitting information and a light emitting unit 364 capable of visually transmitting information are provided on the front surface of the support portion 120. In this case, since it may be designed as a mechanism related to the output unit 360 in the support portion 120 having a predetermined width and width, there is an advantage that the thickness of the battery case 100 may be reduced.

The battery 320 may be disposed on one side of the inside of the battery case 100 along the long side of the battery case 100, and the substrate 140 on which the control unit 300 is installed may be provided as an FPCB (Flexible Printed Circuit Board), such that the thickness of the battery case 100 may be minimized. In addition, the substrate 140 may be formed in an 'L' shape so as not to be overlapped with the battery 320 to be disposed inside the battery case 100. The communication unit 340, the sensor unit 400, and the power processing unit 500 may be mounted on the substrate 140 provided as described above. Further, the positions of parts in charge of each function may be spaced apart from each other so as to increase productivity.

Moreover, in the battery case 100, a hole 130 for the camera may be formed to be corresponded to the position of the rear camera 1c installed in the smartphone 1, so that smooth shooting using the rear camera 1c may be achieved. In addition, the bumper case 200 may be provided with an operation support unit 202 that enables various manipulation devices provided in the smartphone 1 to be used through the bumper case 200. Further, an earphone connection portion 222 communicating with an earphone connection unit of the smartphone 1 may be provided.

According to an embodiment of the present invention having the above-described configuration, the portable terminal case 10 having a skin condition measurement function may be very portable because it is coupled to a smartphone 1 carried by a user. In particular, by configuring the battery case 100 and the bumper case 200 so that there is no significant difference in shape or size from a typical smartphone case, and placing the moisture measurement sensor 412 at one side corner of the front surface, it has an advantage that the user may use it as if using the typical smartphone case without discomfort.

In addition, since the user may detect the contact with the skin by the contact detection unit 420 just by touching the smartphone 1 to the face or by touching a desired portion where the user wants to measure if making a call, so as to measure the content of the skin of the corresponding site, it is possible to measure the skin condition with a very simple and simple operation, which has an advantage of reducing the number of operations and time required by the user. In particular, by providing the bracket 210 on the upper side of the bumper case 200 provided with the receiving speaker 1a, even if the user just puts the smartphone 1 on the face to make a call, the content of moisture of the skin may be measured, so that the skin condition information may be collected even when the user is unconscious.

In addition, the control unit 300 may be configured to transmit data to the smart phone 1 or the server 3 through the communication unit 340 or the portable terminal interface unit 330. Accordingly, there is an effect that the measured results may be stored and monitored even if the user does not perform a separate operation.

Moreover, when the communication unit 340 is provided to use a dedicated network for an IoT provided by a mobile communication company, there are advantages of being able to communicate with low power and at the same time to be interoperable with other IoT-enabled devices connected to the IoT dedicated network.

The following is a list of embodiments of the invention.

Item 1 is a portable terminal case having a skin condition measuring function, comprising: a battery case having a battery therein and attached to the rear surface of the portable terminal; a bumper case coupled to the battery case and surrounding the edges of the portable terminal; a moisture measurement unit for receiving the content of moisture in the skin of a user from a moisture measurement sensor which is provided on the front surface of the bumper case and comes in contact with the skin; a contact detection unit for receiving information on the presence or absence of a contact between the bumper case and the skin from a contact detection sensor for detecting the presence or absence of the contact; an environment measurement unit for receiving surrounding environment information from an environment information measurement sensor for collecting the environment information; and a control unit for collecting the content of moisture and the environment information from the moisture measurement unit and the environment measurement unit according to the detection result of the contact detection unit.

Item 2 is a portable terminal case having a skin condition measuring function according to Item 1, further comprising a communication unit configured to transmit data to a server that provides a service for managing skin condition measurement data, wherein the control unit transmits the content of moisture and the environment information to the server through the communication unit.

Item 3 is a portable terminal case having a skin condition measuring function according to Items 1 and 2, wherein the communication unit further transmits data to the portable terminal, and the control unit transmits the content of moisture and the environment information to at least one of the server and the portable terminal.

Item 4 is a portable terminal case having a skin condition measuring function according to Items 1 to 3, wherein the control unit transmits the content of moisture and the environment information according to a predetermined time interval.

Item 5 is a portable terminal case having a skin condition measuring function according to Items 1 to 4, further comprising a portable terminal interface unit for transmitting the data and power of the battery to the portable terminal.

Item 6 is a portable terminal case having a skin condition measuring function according to Items 1 to 5, wherein the portable terminal interface unit includes: a terminal provided at a lower end portion of the battery case and connected to a connection port provided at a lower side of the portable terminal; and a case connection port configured to couple to a separate cable that is connected to the connection port of the portable terminal, and wherein the battery is chargeable by the cable.

Item 7 is a portable terminal case having a skin condition measuring function according to Items 1 to 6, wherein the bumper case is provided at one end of the upper side or the other side of the bumper case, and includes a bracket formed in parallel with the front surface of the portable terminal, and the moisture measurement unit and the contact detection sensor are disposed in the front surface of the bracket.

Item 8 is a portable terminal case having a skin condition measuring function according to Items 1 to 7, wherein the environment information measurement sensor is disposed on the rear surface of the battery case, and the environment information measurement sensor includes a temperature sensor measuring surrounding temperature and a humidity sensor measuring humidity.

Item 9 is a portable terminal case having a skin condition measuring function according to Items 1 to 8, wherein the lower end portion of the battery case is provided with a support portion for supporting the lower end portion of the portable terminal, the support portion is provided with a portable terminal interface unit for transmitting power of the battery to the portable terminal, and the environment information measurement sensor is disposed on the rear of the support portion.

Item 10 is a portable terminal case having a skin condition measuring function according to Items 1 to 9, further comprising an output unit for transmitting status information to the user.

Item 11 is a portable terminal case having a skin condition measuring function according to Items 1 to 10, wherein the moisture measurement sensor includes: a first electrode oscillating a predetermined frequency; a second electrode surrounding the first electrode and receiving a frequency oscillated from the first electrode; and an insulator insulating the first electrode and the second electrode, and wherein the moisture measurement sensor calculates the content of moisture based on a difference between a value oscillated at the first electrode and a value received at the second electrode.

Item 12 is a portable terminal case having a skin condition measuring function according to Items 1 to 11, wherein the control unit is configured to change the frequency oscillated at the first electrode.

Item 13 is a portable terminal case having a skin condition measuring function according to Items 1 to 12, wherein the control unit receives a command to change the frequency oscillated at the first electrode from the portable terminal and changes the frequency oscillated at the first electrode based on the command.

Item 14 is a portable terminal case having a skin condition measuring function according to Items 1 to 13, wherein the first electrode and the second electrode are concentric, an outer diameter of the first electrode is 1.5 mm, an outer diameter of the second electrode is 6 mm, and an interval between an outer peripheral surface of the first electrode and an inner peripheral surface of the second electrode is 1 mm.

Item 15 is a portable terminal case having a skin condition measuring function, wherein the battery is disposed long along a long side of the battery case on one side inside the battery case, and a substrate provided with the control unit is formed in an 'L' shape so as not to be overlapped with the battery and is disposed inside the battery case.

Item 16 is a portable terminal case having a skin condition measuring function according to Items 1 to 15, wherein the battery case is provided with a camera hole to be corresponded to a position of the rear camera installed in the portable terminal.

As described above, the portable terminal case having the skin condition measurement function according to an embodiment of the present invention has been described as a specific embodiment. However, these are only examples, and the present invention is not limited to these, and should be construed as having the broadest scope according to the basic idea disclosed herein. Those skilled in the art may combine and replace the disclosed embodiments to implement patterns in shapes not explicitly indicated. However, these also do not depart from the scope of the present invention. In addition, those skilled in the art may easily change or modify the disclosed embodiments based on the present specification, and it is obvious that such changes or modifications are within the scope of the present invention.

INDUSTRIAL APPLICABILITY

The invention may be used in the potable terminal and the cosmetics industry.

The invention claimed is:

1. A portable terminal case having a skin condition measuring function, comprising:
    a battery case having a battery therein and attached to the rear surface of the portable terminal;
    a bumper case coupled to the battery case and surrounding the edges of the portable terminal;
    a moisture measurement unit for receiving the content of moisture in the skin of a user from a moisture measurement sensor which is provided on the front surface of the bumper case and comes in contact with the skin;
    a contact detection unit for receiving information on the presence or absence of a contact between the bumper case and the skin from a contact detection sensor for detecting the presence or absence of the contact;
    an environment measurement unit for receiving surrounding environment information from an environment information measurement sensor for collecting the environment information; and
    a control unit for collecting the content of moisture and the environment information from the moisture measurement unit and the environment measurement unit according to the detection result of the contact detection unit,
    wherein the bumper case is provided at one end of the upper side or the other side of the portable terminal, and includes a bracket formed in parallel with the front surface of the portable terminal, and
    wherein the moisture measurement unit and the contact detection sensor are disposed in the front surface of the bracket.

2. The portable terminal case according to claim 1, further comprising a communication unit configured to transmit data to a server that provides a service for managing skin condition measurement data,
    wherein the control unit transmits the content of moisture and the environment information to the server through the communication unit.

3. The portable terminal case according to claim 2, wherein the communication unit further transmits data to the portable terminal, and
    the control unit transmits the content of moisture and the environment information to at least one of the server and the portable terminal.

4. The portable terminal case according to claim 3, wherein the control unit transmits the content of moisture and the environment information according to a predetermined time interval.

5. The portable terminal case according to claim 1, further comprising a portable terminal interface unit for transmitting the data and power of the battery to the portable terminal.

6. The portable terminal case according to claim 5, wherein the portable terminal interface unit includes:
    a terminal provided at a lower end portion of the battery case and connected to a connection port provided at a lower side of the portable terminal; and
    a case connection port configured to couple to a separate cable that is connected to the connection port of the portable terminal, and
    wherein the battery is chargeable by the cable.

7. The portable terminal case according to claim 1, wherein the environment information measurement sensor is disposed on the rear surface of the battery case, and the environment information measurement sensor includes a temperature sensor measuring surrounding temperature and a humidity sensor measuring humidity.

8. The portable terminal case according to claim 7, wherein the lower end portion of the battery case is provided with a support portion for supporting the lower end portion of the portable terminal, the support portion is provided with a portable terminal interface unit for transmitting power of the battery to the portable terminal, and the environment information measurement sensor is disposed on the rear of the support portion.

9. The portable terminal case according to claim 1, further comprising an output unit for transmitting status information to the user.

10. The portable terminal case according to claim 1, wherein the moisture measurement sensor includes:

a first electrode oscillating a predetermined frequency;

a second electrode surrounding the first electrode and receiving a frequency oscillated from the first electrode; and an insulator insulating the first electrode and the second electrode, and wherein the moisture measurement sensor calculates the content of moisture based on a difference between a value oscillated at the first electrode and a value received at the second electrode.

11. The portable terminal case according to claim 10, wherein the control unit is configured to change the frequency oscillated at the first electrode.

12. The portable terminal case according to claim 11, wherein the control unit receives a command to change the frequency oscillated at the first electrode from the portable terminal and changes the frequency oscillated at the first electrode based on the command.

13. The portable terminal case according to claim 10, wherein the first electrode and the second electrode are concentric, an outer diameter of the first electrode is 1.5 mm, an outer diameter of the second electrode is 6 mm, and an interval between an outer peripheral surface of the first electrode and an inner peripheral surface of the second electrode is 1 mm.

14. The portable terminal case according to claim 1, wherein the battery is disposed along a long side of the battery case on one side inside the battery case, and a substrate provided with the control unit is formed in an 'L' shape so as not to be overlapped with the battery and is disposed inside the battery case.

15. The portable terminal case according to claim 14, wherein the battery case is provided with a camera hole to be corresponded to a position of the rear camera installed in the portable terminal.

* * * * *